United States Patent [19]
Dinh et al.

[11] Patent Number: 5,733,255
[45] Date of Patent: Mar. 31, 1998

[54] THERMOPILE POWERED TRANSDERMAL DRUG DELIVERY DEVICE

[75] Inventors: Steven M. Dinh, Briarcliff Manor, N.Y.; Sietse E. Wouters, Ettingen, Switzerland; Joseph R. Sclafani, Jr., Baltimore, Md.

[73] Assignee: Novartis Finance Corporation, New York, N.Y.

[21] Appl. No.: 729,969

[22] Filed: Oct. 15, 1996

Related U.S. Application Data

[60] Provisional application No. 60/005,654, Oct. 18, 1995.

[51] Int. Cl.$^6$ .................................................. A61N 1/30
[52] U.S. Cl. .......................... 604/20; 424/448; 424/449; 607/2; 607/75
[58] Field of Search .......................... 604/20; 607/75, 607/2; 424/448, 449

[56] References Cited

U.S. PATENT DOCUMENTS

| | | | |
|---|---|---|---|
| 3,598,122 | 8/1971 | Zaffaroni | 128/268 |
| 3,598,123 | 8/1971 | Zaffaroni | 128/268 |
| 3,794,910 | 2/1974 | Ninke et al. | 324/30 |
| 3,991,755 | 11/1976 | Vernon et al. | 182/172.1 |
| 4,019,510 | 4/1977 | Ellis | 128/172.1 |
| 4,031,894 | 6/1977 | Urquhart et al. | 128/268 |
| 4,106,279 | 8/1978 | Martin et al. | 58/23 |
| 4,141,359 | 2/1979 | Jacobsen et al. | 128/172.1 |
| 4,213,292 | 7/1980 | Dolezal et al. | 368/204 |
| 4,242,968 | 1/1981 | Schaidl et al. | 108/20 |
| 4,250,878 | 2/1981 | Jacobsen et al. | 128/207.21 |
| 4,262,003 | 4/1981 | Urquhart et al. | 424/267 |
| 4,320,477 | 3/1982 | Baumgartner | 368/64 |
| 4,325,367 | 4/1982 | Tapper | 128/207.21 |
| 4,371,269 | 2/1983 | Sutter | 368/205 |
| 4,398,545 | 8/1983 | Wilson | 128/798 |
| 4,457,748 | 7/1984 | Lattin et al. | 604/20 |
| 4,474,570 | 10/1984 | Ariura et al. | 604/20 |
| 4,722,726 | 2/1988 | Sanderson et al. | 604/20 |
| 4,744,787 | 5/1988 | Phipps et al. | 604/20 |
| 4,935,345 | 6/1990 | Guilbeau et al. | 435/14 |
| 5,006,108 | 4/1991 | LaPrade | 604/20 |
| 5,013,293 | 5/1991 | Sibalis | 604/20 |
| 5,023,085 | 6/1991 | Francoeur et al. | 424/449 |
| 5,135,480 | 8/1992 | Bannon et al. | 604/20 |
| 5,147,297 | 9/1992 | Myers et al. | 604/20 |
| 5,203,768 | 4/1993 | Haak et al. | 604/20 |
| 5,207,752 | 5/1993 | Sorenson et al. | 604/20 |
| 5,310,404 | 5/1994 | Gyrory et al. | 604/20 |
| 5,312,326 | 5/1994 | Myers et al. | 604/20 |
| 5,314,502 | 5/1994 | McNichols et al. | 604/20 |

FOREIGN PATENT DOCUMENTS 1123615  5/1982  Canada.

*Primary Examiner*—D. Gabrielle Phelan
*Attorney, Agent, or Firm*—Gregory D. Ferraro

[57] ABSTRACT

A transdermal drug delivery device has a drug containing element containing a drug which is preferably charged and first and second electrodes for conducting a current flow through the drug containing element. The current flow causes the drug to be released from the drug containing element and to permeate through the skin of a user to which the device has been fixed. A power source is connected to the first and second electrodes for providing the energy necessary to generate the current flow. The power source comprises a thermocouple or thermopile having two different poles which are connected to the first and/or second electrodes, whereby a self-contained drug delivery device is formed which provides the energy necessary for generating the current flow by means of a difference in temperature of the skin of the user and the ambient air (environment), thus providing a device free of batteries, accumulators or other external energy sources.

20 Claims, 8 Drawing Sheets

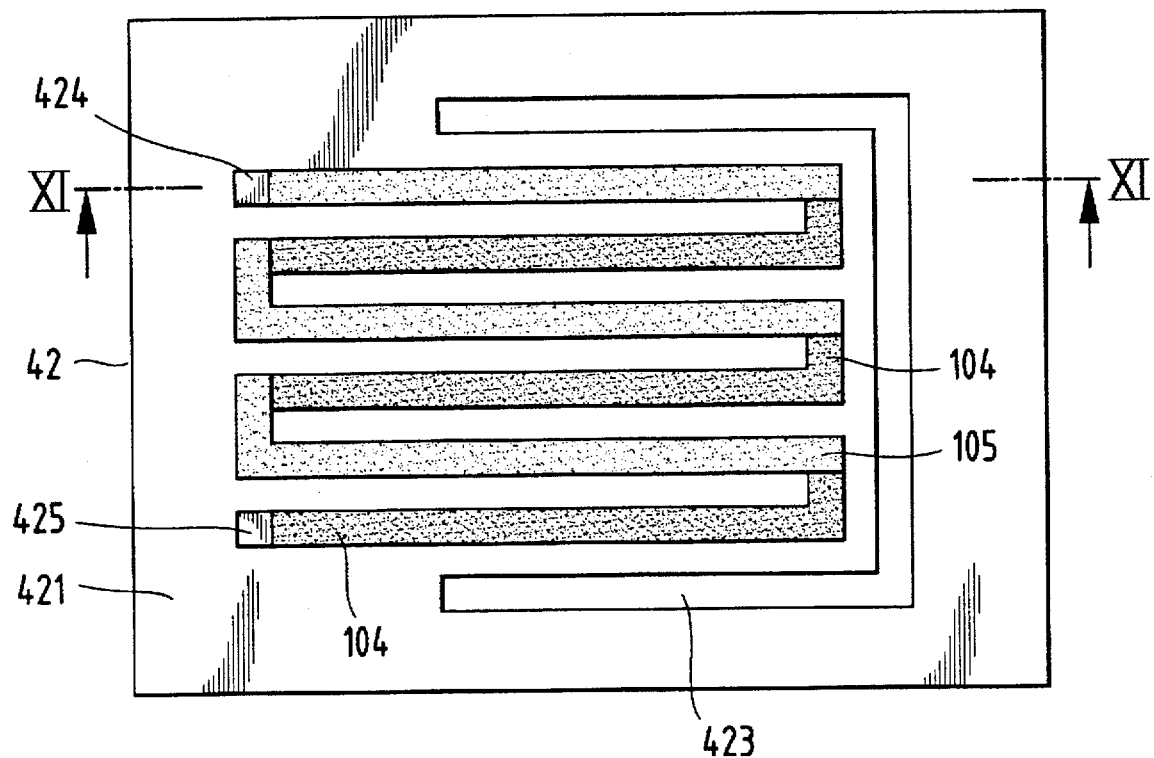

THERMOPILE POWERED TRANSDERMAL DRUG DELIVERY DEVICE

CROSS-REFERENCE TO RELATED APPLICATION

This application claims the benefit of U.S. Provisional Application No. 60/005,654, filed Oct. 18, 1995.

BACKGROUND OF THE INVENTION

1. Field of the Invention

The present invention relates to transdermal drug delivery devices generally, and to a thermopile powered transdermal drug delivery device in particular.

2. Description of the Related Art

Transdermal drug delivery has been known for more than fifteen years and a great number of patent applications have been filed in connection with that technology. Devices representative for that technology are described in U.S. Pat. No. 3,598,122; U.S. Pat. No. 3,598,123; U.S. Pat. No. 4,031,894; U.S. Pat. No. 4,201,211 and U.S. Pat. No. 4,262,003; all of which are incorporated herein by reference. Drugs which have been marketed in transdermal systems include nitroglycerin, clonidine, scopolamine, estradiol, estradiol/NETA combination, fentanyl and nicotine, among others.

Early on it was recognized that most drugs did not readily pass through the skin and skin permeation enhancers were needed in order to be able to deliver the drug in a therapeutically effective manner and to allow the system to control the drug delivery profile. This shift in control from the skin to the system reduces inter- and intra-patient flux variability. Additionally, the size of the patches to be used had limitations based on the location of application and the aesthetic view of the patient being able to use the patches without others knowing about it. In other instances, the active agent exists as a charged species at formulation conditions which are necessary due to other requirements. These charged species do not pass through the skin barrier with any degree of efficiency even with the help of permeation enhancer molecules.

To deal with the area of transdermal administration of charged species in a more complete and efficient manner, iontophoretic delivery was developed. Iontophoresis, according to Dorland''s Medical Dictionary, is the introduction, by means of electric current, of ions of soluble salts into the tissues of the body for therapeutic purposes. Iontophoretic devices have been known since the early 1900's. With greater emphasis and maturing of the transdermal field generally during the late 1970's to the present, the iontophoretic delivery of drugs has taken on greater interest. During iontophoresis, an electric field is used to assist in and control the delivery of drugs through the skin. The electric field induces charged species to migrate toward one electrode or away from that electrode toward another, opposite electrode (which is oppositely charged). When an electro-chemical circuit across the skin is established by incorporating the physiological electrolytes, the delivery of drug due to the electric potential can be exploited. In addition, electric fields applied to the skin have also been found to increase, although less dramatically, the flux of some uncharged species through skin. Hence, iontophoretic transdermal drug delivery offers substantial promise for the administration of a wide variety of drug substances through the skin, which otherwise could not be efficaciously administered by transdermal or other conventional routes.

Representative iontophoretic systems and components are described in U.S. Pat. No. 3,991,755; U.S. Pat. No. 4,141,359; U.S. Pat. No. 4,398,545; U.S. Pat. No. 4,250,878; U.S. Pat. No. 4,474,570; U.S. Pat. No. 5,314,502; U.S. Pat. No. 5,312,326; U.S. Pat. No. 5,310,404; U.S. Pat. No. 5,203,768; U.S. Pat. No. 5,147,297; U.S. Pat. No. 5,013,293; U.S. Pat. No. 5,135,480; U.S. Pat. No. 4,722,726; U.S. Pat. No. 5,207,752; U.S. Pat. No. 4,457,748; U.S. Pat. No. 4,744,787; U.S. Pat. No. 5,006,108; U.S. Pat. No. 3,794,910; U.S. Pat. No. 4,242,968; U.S. Pat. No. 4,301,794; U.S. Pat. No. 4,019,510; U.S. Pat. No. 4,325,367; and U.S. Pat. No. 5,023,085; among others, all of which are incorporated herein by reference. Additionally, thermopiles on flexible substrates are know from U.S. Pat. No. 4,935,345. Watches powered by means of thermopiles are known, for example, from CH 604,249; CH 613 087; CA 1,123,615; GB 2,071,366; GB 2,076,568.

The essential components of the iontophoretic systems described in the above identified patents include the drug containing element, suitable adhesives to have the complete system or device adhere to the skin, the drug electrode establishing electrical contact to the drug solution in the drug containing element, a further electrode for a return path of the current, a source of electrical energy, appropriate electrical connectors between the various components and electronic circuitry to control the current or voltage.

Any kind of iontophoretic device needs an electrical power source to generate a constant or pre-determined time-varying current or voltage. Usually, the mains or one or more batteries are used to power an iontophoretic device. The mains as a power source has the obvious disadvantage of restraining and potentially endangering the patient. The batteries, while having the advantage of being portable, have the disadvantage of containing harmful materials, like anode materials (Pb, Cd, Zn, Mg, Li), cathode materials ($PbO_2$, AgO, $Ag_2$, $MnO_2$, $SO_2$) and electrolytes (KOH, NaOH, $NH_4Cl$, $ZnCl_2$, $MgBr_2$, organic solvents). These materials are harmful to the patient when leakage or breaking occurs during use, they are harmful to the environment after disposal, and they may damage the delivery system and disrupt normal administration. Modern batteries are prevented from leakage and rupture by hermetically sealing the battery materials in a metal container. This container is relatively thick and stiff and is therefore not very suitable to be worn on a patient's skin.

OBJECTS OF THE INVENTION

It is therefore an object of the invention to provide a transdermal drug delivery device which does not require batteries or a connection to the mains.

It is a further object of the invention to provide a transdermal drug delivery device which eliminates the concern for having batteries contained therein, since battery leakage can cause damage to the patient and/or to the device. Furthermore, disposal of devices having batteries contained therein is problematic with respect to the environment.

Still a further object of the invention is to simplify manufacture of transdermal drug delivery devices, thereby reducing the costs of manufacture. This holds particularly for devices in which the batteries are located in the disposable part of the patch.

SUMMARY OF THE INVENTION

These and other objects of the present invention can be achieved by a transdermal drug delivery device as proposed and claimed in this application, which incorporates a thermocouple or thermopile as part of the transdermal patch itself, so that the difference between the body temperature of the wearer and the ambient temperature (environment) gives rise to an electric potential sufficient to result in an effective iontophoretic-aided delivery of the active agent (drug) contained in the device.

The general concept underlying the present invention, therefore, is the use and the incorporation of a thermocouple or thermopile into a transdermal drug delivery device in order to take advantage of differences between the body temperature and the temperature of the ambient air to generate an electrical voltage or current to aid in the transdermal delivery of drugs to a patient. Thermopiles, when compared to batteries, improve the safety, reliability and ease of disposal of the devices, while maintaining the elegance and patient acceptance of the overall device exhibited by non-iontophoretic transdermals.

BRIEF DESCRIPTION OF THE DRAWINGS

FIG. 10 shows a top view on a further embodiment of a thermopile.

FIG. 11 shows a cross section along line XI—XI of the thermopile of FIG. 10.

DETAILED DESCRIPTION OF THE PREFERRED EMBODIMENTS

Figure 1:
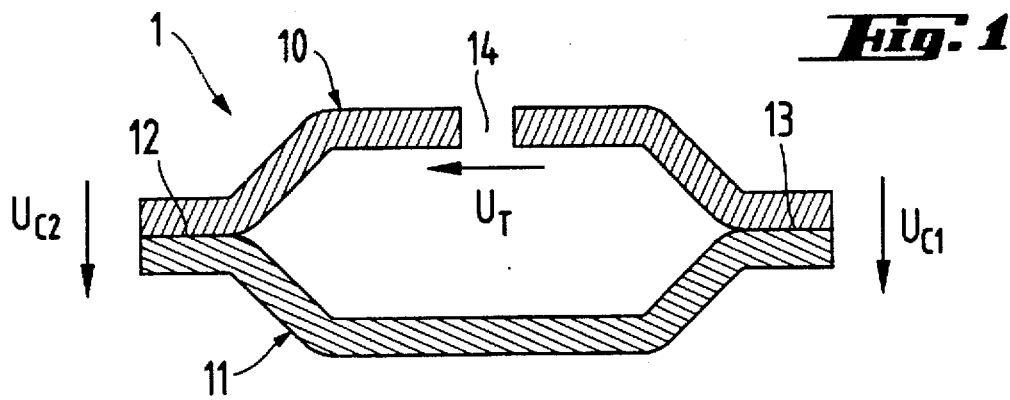
FIG. 1 is a schematic representation of a thermocouple.

FIG. 1 shows a schematic representation of a conventional thermocouple 1 in a simplified form. This schematic representation helps to understand the fundamental way in which thermocouples work. The shape of the thermocouple shown in FIG. 1 has only been chosen to simplify explanation of the way in which thermocouples work. As will be seen below, the shape of the thermocouples may vary. Essentially, the thermocouple shown in FIG. 1 comprises two elements 10 and 11 each made of different materials which are electrically conductive. The elements have two areas 12 and 13 where they are in contact. Element 10 is provided with a gap 14 between the two areas of contact (so that element 10 comprises two halves which are electrically isolated from each other), while element 11 is continuous therebetween. It is assumed for example, that on the left hand side the ends of the two elements 10 and 11 contacting each other are both exposed to a first temperature, while on the right hand side the other ends of the elements 10 and 11 are exposed to a second temperature. The first temperature is, for example, lower than the second temperature. As a consequence, the contact voltages $U_{c1}$ and $U_{c2}$ between the two elements 10 and 11 at the two areas of contact are different. Since there are no further voltage sources in the loop, and since the sum of voltages in a closed loop through the two elements has to be zero, the voltage $U_T$ across gap 14 is equal to the difference of the two voltages at the areas of contact. This voltage $U_T$ can be used, as will be shown in detail below, to power a transdermal drug delivery device according to the instant invention. Connecting a number of thermocouples in series results in a thermopile in which the electrical potentials of the individual thermocouples add up to the thermopile electrical potential. Thermopile powered transdermal drug delivery devices according to the instant invention therefore do not need any additional electrical power source, neither the mains nor any batteries.

Thermocouples and thermopiles have been used in a variety of contexts to generate a voltage, a current or electric power based on temperature differences. Thermocouples essentially respond to temperature differences by generating a small electrical potential. That small potential can either be used as a measure of temperature or of a temperature difference or it can be used as a source of electrical energy. Generally, the electrical power generated by a single thermocouple is insufficient for most uses of the thermocouple as a source of electrical energy. However, if the required power is sufficiently low, a single thermocouple can also be used as an energy source. For that reason, thermopiles are often used. A thermopile is a group of thermocouples connected such that their individual electrical potentials add up (series connection). Thermopiles, when compared to batteries, improve the safety, reliability and ease of disposal of the devices, while maintaining the elegance and patient acceptance normally exhibited by non-iontophoretic transdermals.

Figure 2:
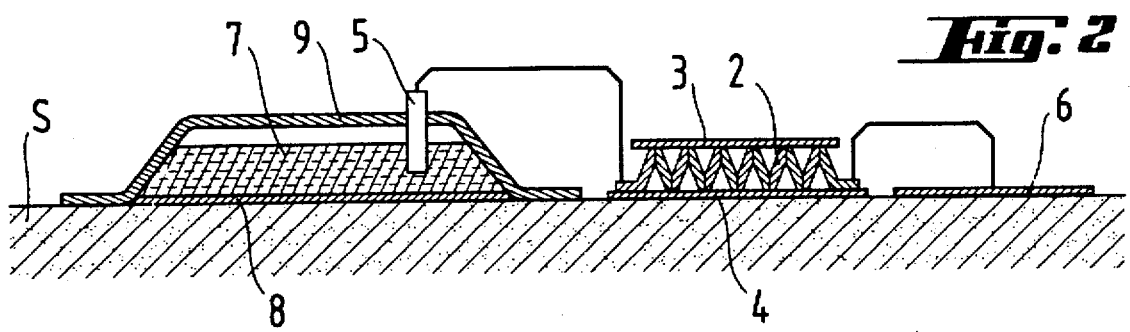
FIG. 2 is a schematic representation of the essential elements of a thermopile transdermal drug delivery device according to the instant invention.

FIG. 2 shows schematically the essential elements of a thermopile transdermal drug delivery device (transdermal patch) according to the instant invention. A thermopile 2 comprising several thermocouples arranged between two thermally conductive plates 3 and 4 is connected at its two poles (ends) with a first electrode 5 and a second electrode, which is referenced to as counter-electrode 6 hereinafter. The thermocouples shown in FIG. 2 are, for example, columnar elements (and therefore different in shape from the thermocouple in FIG. 1) connected in series to form a thermopile. The counter-electrode 6 is in contact with the skin S of the user. The first electrode is in contact with a drug containing element 7, which itself is in contact with the skin S of the user either directly or via a permeable membrane 8. Drug containing element 7 may be any suitable element known in the transdermal art, including, but not limited to, a reservoir, a matrix, a gel, particularly a hydrogel, or a non-woven. The backing material of the drug containing element is a preferably impermeable layer 9. Especially when the content of the drug containing element is a liquid (e.g. a solution), means (preferably a membrane) for retaining the liquid in the drug containing element 7 are required in order to prevent spillage of the liquid contained. Plate 3 is in contact with the ambient air (environment) while plate 4 is in contact with the skin S of the user to which the patch is applied. Since the temperature of air is different from the temperature of the skin, a voltage is generated by thermopile 2. This voltage is used to cause the drug to be delivered through membrane 8 into the skin of the user. Counter-electrode 6 provides the return pathway thereby completing the circuit.

Figure 3:
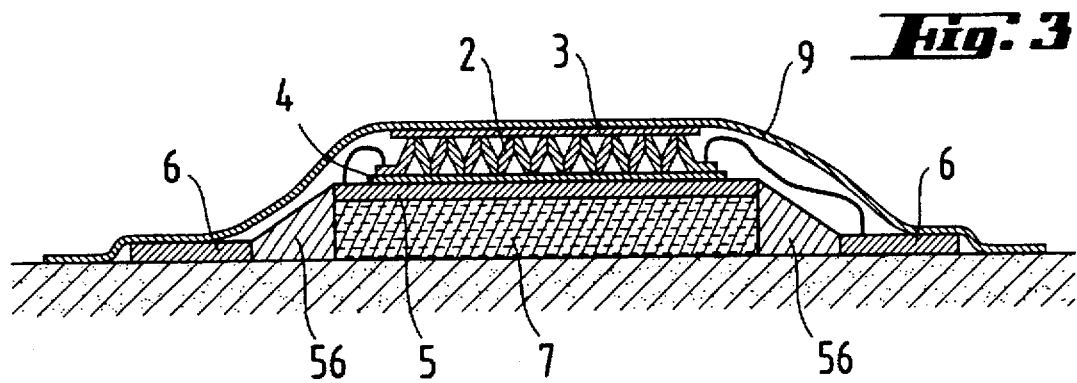
FIG. 3 is a section through an embodiment of a thermopile transdermal drug delivery device according to the present invention having all necessary components contained therein.

FIG. 3 shows a section through a practical embodiment of a transdermal drug delivery device according to the instant invention (any sealing foils for protecting the whole device during storage have been omitted for the sake of clarity). The device shown here is a self-contained transdermal patch. Like numbers are assigned to elements corresponding to like elements of the schematic representation of FIG. 2. In the embodiment shown in FIG. 3, the content of drug containing element 7 is thermally conductive. Electrode 5 is also made of a thermally conductive material. Therefore, electrode 5 and plate 4 of thermopile 2, which is located on top of electrode 5, have essentially the same temperature as skin S, whereas plate 3 has a temperature near that of ambient air. Furthermore, there is no membrane between the drug containing element 7 and the skin S. Drug containing element 7 may, for example, comprise a non-woven or a gel, specifically a hydrogel. Counter-electrode 6 is arranged along the periphery of the patch. Between electrode 5 and counter-electrode 6, an insulating material 56 is arranged which does not only prevent a short circuit but also prevents diffusion between drug containing element 7 and counter-electrode 6. Furthermore, insulating material 56 in this embodiment also defines the shape of drug containing element 7. Backing layer 9 completes the self-contained patch. Since the temperatures of plates 4 and 3 are different, thermopile 2 generates a voltage between its two poles (ends). The poles are connected to electrode 5 and counter-electrode 6, respectively, by any suitable means (e.g. wires or printed strips on the inside of backing layer 9). In the case when the drug to be delivered is charged, it is clear that the poles are connected to electrode 5 and counter-electrode 6 in such a way as to ensure that the charged drug is transported from drug containing element 7 into skin S of the user. In order to fix the patch on the skin, some or all parts contacting the skin or only backing layer 9 may be self-adhesive or can be provided with an adhesive layer to allow them to adhere to the skin of the user who applies the patch.

Figure 4:
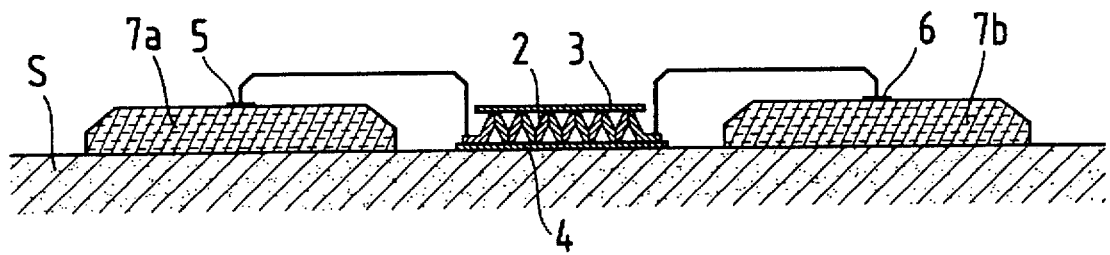
FIG. 4 is a schematic representation of a further embodiment of a thermopile transdermal drug delivery device according to the instant invention.
Figure 14:
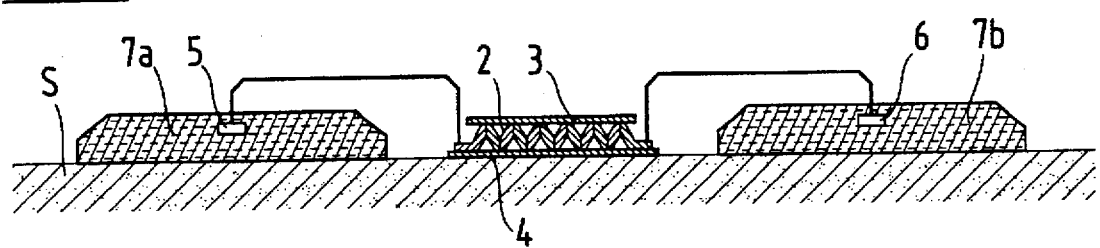
FIG. 14 shows the embodiment of FIG. 4 with the electrodes arranged in the drug containing elements.

FIG. 4 shows schematically a further embodiment of the transdermal drug delivery device according to the instant invention. In order to emphasize the differences of the device shown in FIG. 4, when compared to the devices described above, only a few elements are shown. Plate 4 is arranged to contact the skin S while plate 3 is in contact with the ambient air. The main difference of the embodiment in FIG. 4 is that two drug containing elements 7a and 7b are provided. On top of the drug containing elements 7a and 7b, the electrode 5 and counter-electrode 6 can be provided or the electrodes can be provided in the drug containing elements 7a and 7b (FIG. 14).

It is possible that in both drug containing elements the same drug is provided. This is especially useful for instances in which the temperature of the ambient air is sometimes higher, sometimes lower, than the temperature of the skin (e.g. in countries having a hot climate). In such instances the delivery of the medicament is independent from whether the temperature of the ambient air is higher or lower than the temperature of the skin. A further advantage of this embodiment is that in cases in which the temperature of the ambient air is always higher or lower than that of the skin (usually the temperature of the ambient air is lower than that of the skin) two oppositely charged drugs can be delivered at the same time, one drug being contained in drug containing element 7a while the other is contained in drug containing element 7b.

Figure 5:
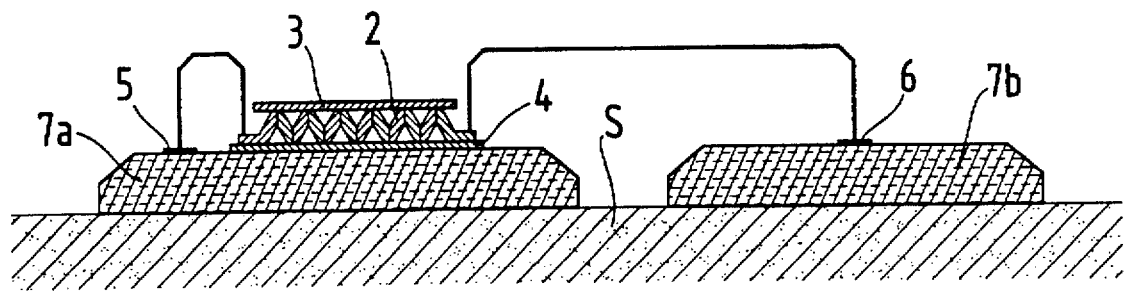
FIG. 5 shows an alternate version of the device of FIG. 4, where the thermopile has been placed on top of an electrode which itself is located on top of a thermally conductive drug containing element.
Figure 15:
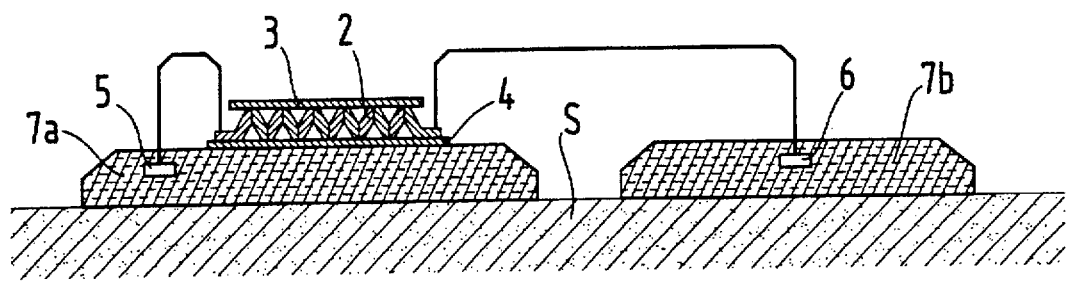
FIG. 15 shows the embodiment of FIG. 5 with the electrodes arranged in the drug containing elements.

In FIG. 5 a further embodiment of the transdermal drug delivery device is shown which is to a large extent similar to that shown in FIG. 4. The essential difference is that plate 4 is arranged on top of one of the drug containing elements. For example, plate 4 is arranged on top of drug containing element 7a. This embodiment is advantageous over that shown in FIG. 4 in that the total area of the patch is reduced. However, it is a requirement for this embodiment that the drug containing element is thermally conductive. Electrode 5 and counter-electrode 6 can be arranged either on top of the drug containing elements 7a and 7b (FIG. 5) or they can be arranged in the drug containing element (FIG. 15).

Figure 6:
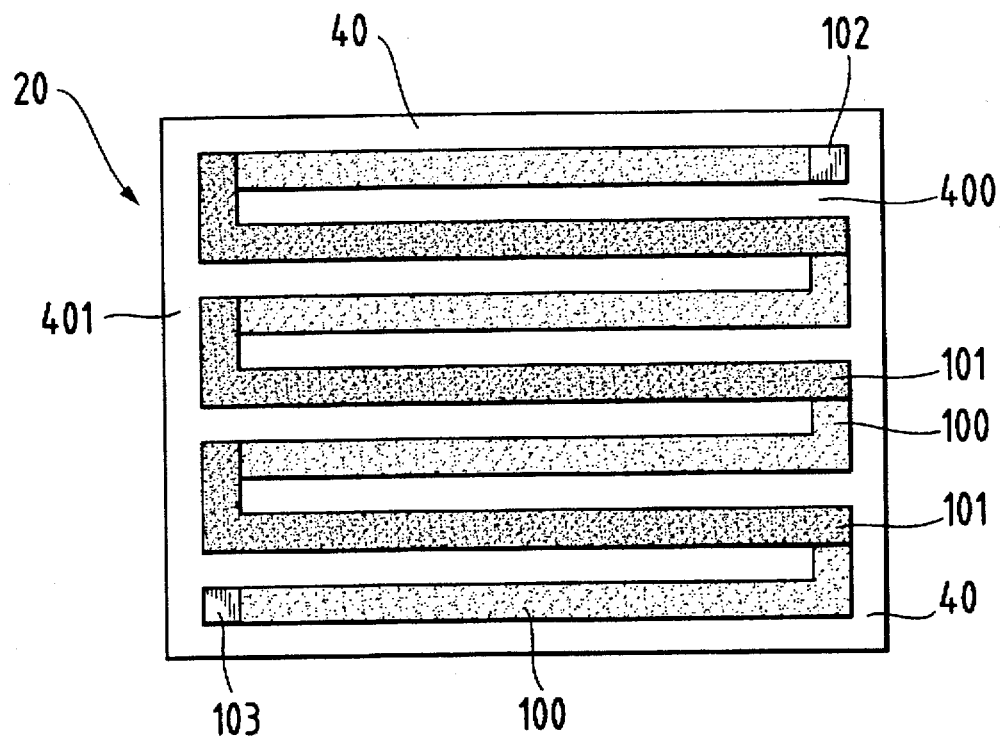
FIG. 6 shows a top view of an embodiment of a thermopile fabricated on a thin flexible thermally conductive substrate.

FIG. 6 shows a top view of an embodiment of a thermopile 20 fabricated on a thin flexible thermally conductive material. The thin flexible and thermally conductive (but electrically nonconductive) material may be, for example, a mylar or polyimide foil 40. On this foil several thermocouples are provided in series connection. The thermocouples are made of first and second electrically conductive materials 100 and 101 and are arranged in alternating sequence in a snake-like manner. At one end of the snake there is provided a first electrical contact or pole 102 while a second electrical contact or pole 103 is provided at the other end of the snake. In order to generate a voltage, one side portion 400 (right hand side in FIG. 6) of the thermally conductive foil 40 is exposed to a first temperature while the other side portion 401 (left hand side in FIG. 6) is exposed to a second temperature. The various voltages generated by the thermocouples add up to the voltage generated by the whole thermopile 20. Since the thermocouple materials as well as the electrical contacts are thin and flexible, the whole structure is flexible and can adapt to the surface to which it is attached.

Figure 7:
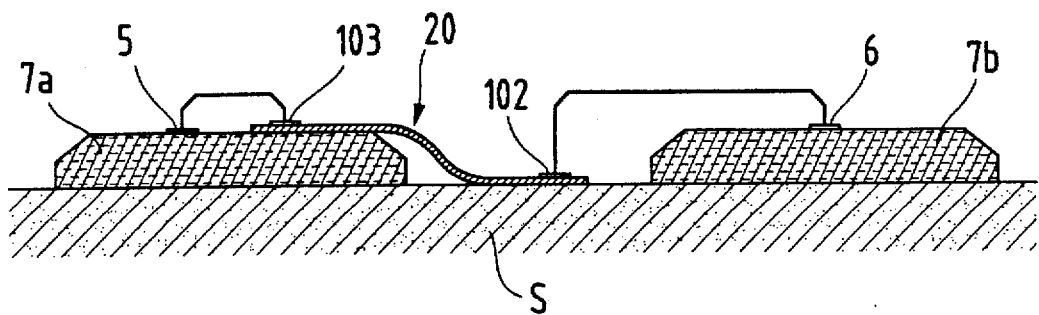
FIG. 7 shows a further embodiment of a transdermal device according to the instant invention comprising the flexible thermopile of FIG. 6.
Figure 16:
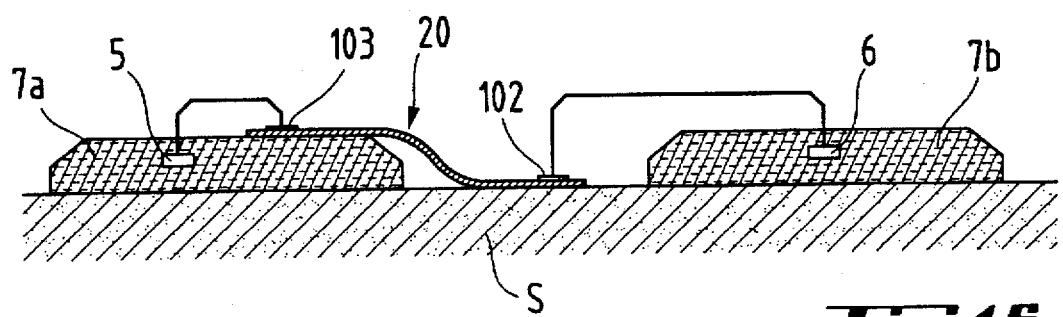
FIG. 16 shows the embodiment of FIG. 7 with the electrodes arranged in the drug containing elements.

FIG. 7 shows a further embodiment of the transdermal drug delivery device according to the instant invention. The embodiment shown there comprises the flexible thermopile 20 which has been explained in detail with reference to FIG. 6 (see preceding paragraph). Furthermore, this embodiment comprises two drug containing elements 7a and 7b, similar to the embodiments described with reference to FIG. 4 and FIG. 5. The flexible thermopile 20 is bent so that side portion 401 (FIG. 6) is arranged on top of drug containing element 7a while the other side portion 400 is in contact with the skin S of the user. Pole 103 is connected to the first electrode 5 which is arranged on top of drug containing element 7a while pole 102 is connected to the second or counter-electrode 6 which is arranged on top of drug containing element 7b. Alternatively, electrode 5 and counter-electrode 6 can be arranged in drug containing element 7a and 7b as it is shown in FIG. 16. It is clear to the skilled reader that drug containing element 7a is essentially thermally insulating, that is to say thermally non-conductive. As already discussed with reference to FIG. 4 and FIG. 5, it is either possible to provide the same drug in both drug containing elements 7a and 7b or to provide different drugs. The advantage of such device is apparent when it is used as a transdermal patch: the complete patch remains flexible, which is important with respect to user compliance and with respect to reliable adhesion of the patch to the skin.

Figure 8:
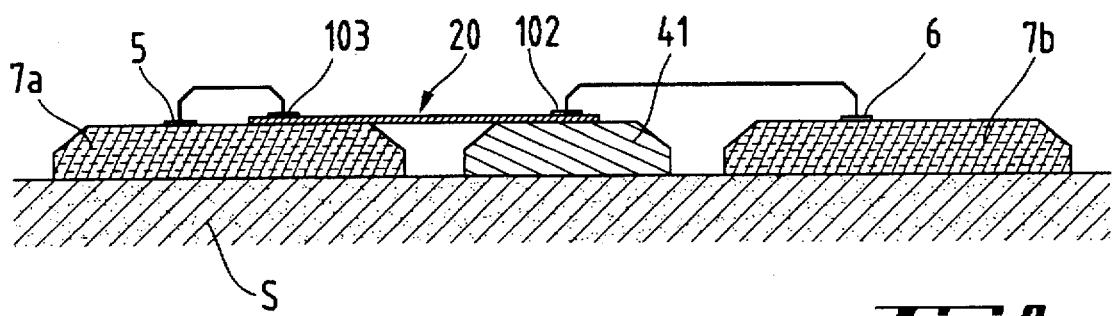
FIG. 8 shows a further embodiment of a transdermal device according to the instant invention comprising the flexible thermopile of FIG. 6.
Figure 17:
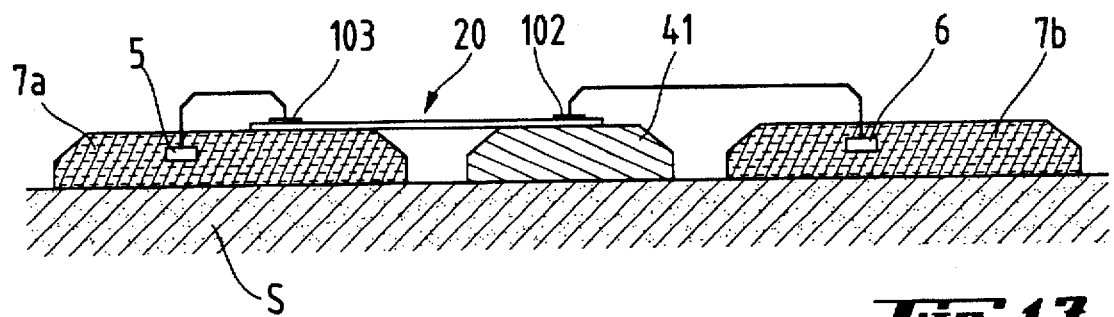
FIG. 17 shows the embodiment of FIG. 8 with the electrodes arranged in the drug containing elements.

FIG. 8 represents a further embodiment of the transdermal drug delivery device in accordance with the instant invention. The embodiment shown here differs from that shown in FIG. 7 essentially in that the side portion 400 (see FIG. 6) is arranged on top of a supporting member 41. Supporting member 41 can be made of a thermally insulating material, that is to say it is thermally non-conductive. In this case it is required that drug containing element 7a consists of a thermally conductive material. Supporting member 41 can also be made of a thermally conductive material. In this case, drug containing element 7a must consist of a thermally nonconductive material. In both cases, the need of bending flexible thermopile 20 is eliminated. Additionally, any limitations regarding thermal conductivity of the content of the drug containing element 7a or of the material of the first electrode can be overcome. Electrode 5 as well as counter-electrode 6 can be arranged on top of drug containing elements 7a and 7b, as it is shown in FIG. 8, or they can be arranged in drug containing elements 7a and 7b, as it is shown in FIG. 17.

Figure 9:
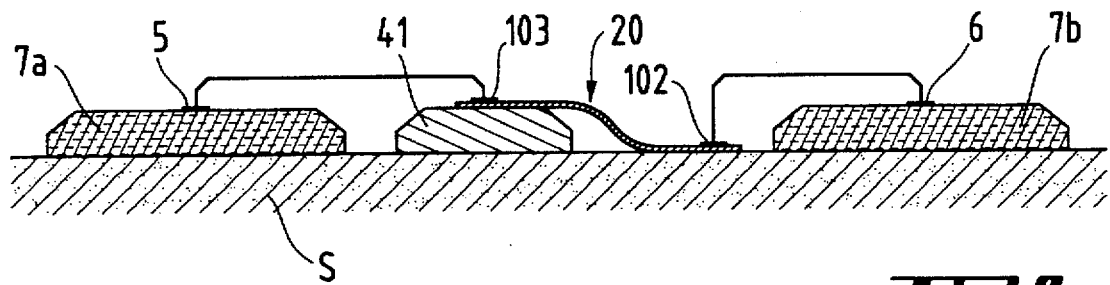
FIG. 9 shows still a further embodiment of a transdermal device according to the instant invention comprising the flexible thermopile of FIG. 6.
Figure 18:
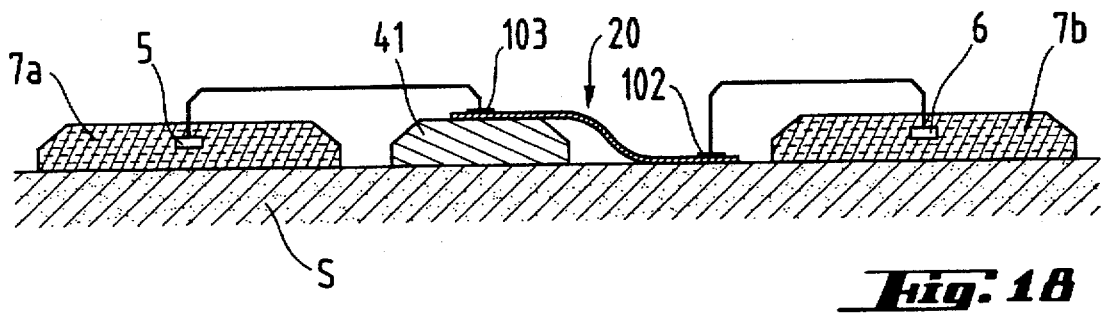
FIG. 18 shows the embodiment of FIG. 9 with the electrodes arranged in the drug containing elements.

FIG. 9 represents a further embodiment of the transdermal drug delivery device according to the instant invention. This embodiment differs from that described with reference to FIG. 8 in that side portion 400 is arranged to be in contact with the skin S, while side portion 401 is located on top of supporting member 41. It is clear for the skilled reader, that in this case supporting member 41 consists of a thermally insulating material. Again, electrode 5 and counter-electrode 6 can either be arranged on top of drug containing elements 7a and 7b, as it is shown in FIG. 9, or they can be arranged in drug containing elements 7a and 7b, as it is shown in FIG. 18.

In FIG. 10 and in FIG. 11 a further embodiment of a thermopile is shown, to which reference number 21 is generally assigned. FIG. 10 represents a top view while FIG. 11 represents a sectional view along line XI—XI in FIG. 10. Thermopile 21 comprises a thin plate 42 which is preferably made of silicon. The silicon plate has a comparatively thick rim 420 around the periphery and a comparatively thin cantilever 422 extending towards the center of the device. Cantilever 422 is mechanically connected with side portion 421 whereas there is a gap 423 between cantilever 422 and the other three side portions of plate 42. A number of thermocouples, which are made of different materials 104 and 105, are arranged in series connection in a snake-like manner on the top surface of silicon plate 42. The contact areas of adjacent thermocouples are alternately located on the rim 420 and at the opposite end of cantilever 422 near gap 423. Electrical contacts 424 and 425 are both located on rim 420, but at different ends of the snake. When there exists a temperature difference between the rim 420 and the tip of cantilever 422, a voltage is generated between electrical contacts 424 and 425 which is the sum of the individual voltages generated by the thermocouples. The advantages of silicon thermopiles are that they are very small (e.g. the area is smaller than 1 cm$^2$) and thin (e.g. the thickness is smaller than 0.5mm) and that they are suited for mass production. A typical silicon thermopile consists of a comparatively thick rim (about 0.3mm) and a comparatively thin cantilever (about 0.01mm).

Figure 12:
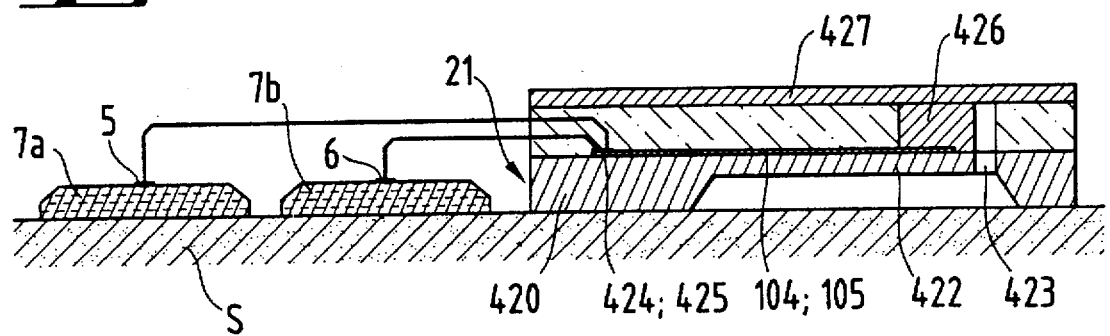
FIG. 12 shows a further embodiment of a transdermal device according to the instant invention comprising the thermopile of FIG. 10.
Figure 19:
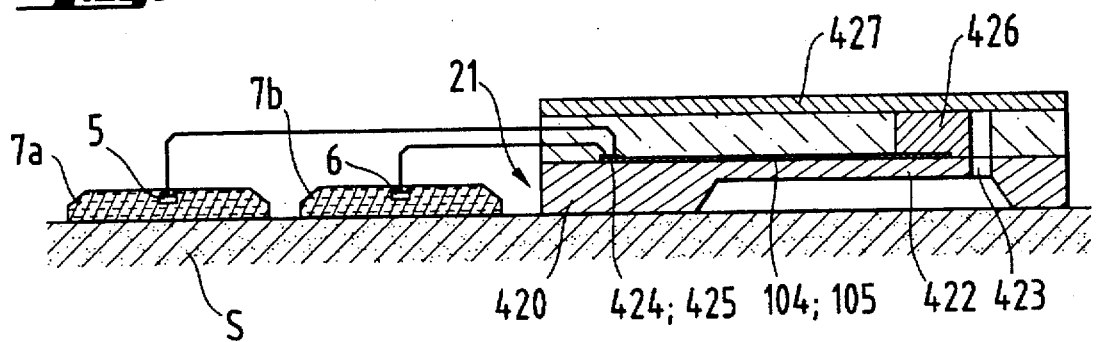
FIG. 19 shows the embodiment of FIG. 12 with the electrodes arranged in the drug containing elements.

FIG. 12 shows an embodiment of a transdermal drug delivery device according to the instant invention using the thermopile 21 that has been described with reference to FIG. 10 and FIG. 11 (see preceding paragraph). This embodiment comprises two drug containing elements 7a and 7b and a first electrode 5 arranged on top of drug containing element 7a and a counterelectrode 6 arranged on top of drug containing element 7b. Additionally, the device shown in FIG. 12 comprises thermopile 21. Rim 420 is arranged to be in contact with the skin S of the user, while the tip of cantilever 422 is connected via a thermally conductive piece 426 to a thermally conducting sheet 427 which can, for example, be incorporated in the backing layer of the transdermal device, and which is in contact with the ambient air, thus cooling down the tip of the cantilever 422. In order to make the system mechanically rugged the space between the thermopile 21 and the thermally conductive sheet 427 is filled with a thermally and electrically insulating support material. The electrical contacts 425 and 424 are connected to the first electrode 5 and to the counter-electrode 6, respectively, both located on top of drug containing elements 7a and 7b. Alternatively, as shown in FIG. 19, electrode 5 and counter-electrode 6 may be arranged in the drug containing elements 7a and 7b.

Figure 13:
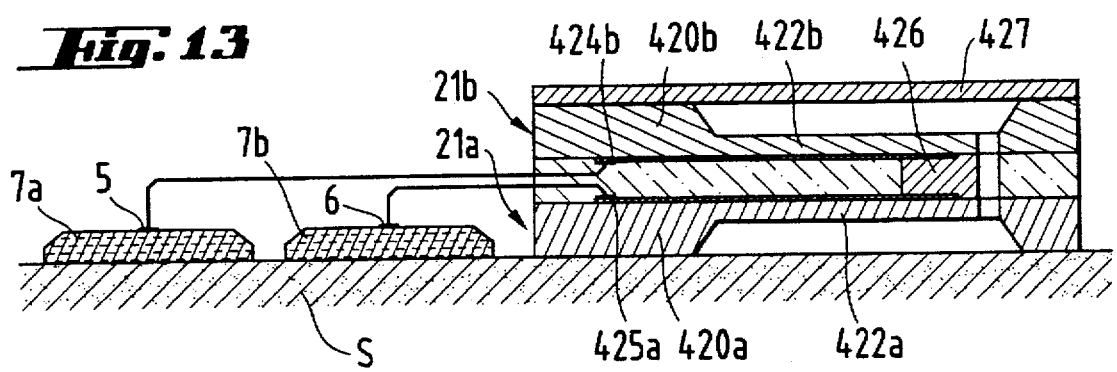
FIG. 13 shows still a further embodiment of a transdermal device according to the instant invention comprising two of the thermopiles shown in FIG. 10.
Figure 20:
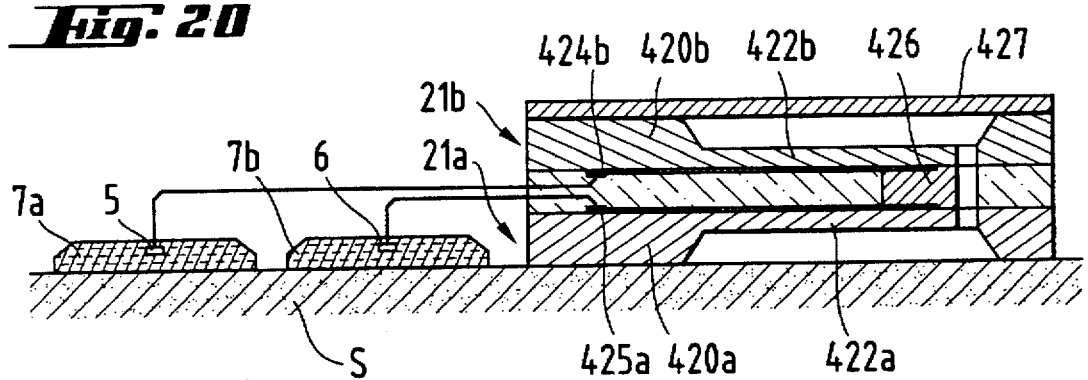
FIG. 20 shows the embodiment of FIG. 13 with the electrodes arranged in the drug containing elements.

Still a further embodiment of the transdermal drug delivery device according to the instant invention is shown in FIG. 13. This is an embodiment comprising a dual thermopile configuration, that is to say it comprises two thermopiles 21a and 21b, the cantilever tips 422a and 422b of which are connected by means of a thermally conductive piece 426. The rim of the upper thermopile 21b is connected to a thermally conductive sheet 427, which can be made of a thermally conductive polymer or which can be a metal foil, and which is in contact with the ambient air. In this embodiment the temperature decreases starting from rim 420a, which is in contact with the skin S, to cantilever 422a, to cantilever 422b, down to the lowest temperature at rim 420b (provided that the ambient temperature is lower than the temperature of the skin). In this case the electrical contacts 425a and 424b are used to supply the electrodes 5 and 6 arranged on top of drug containing elements 7a and 7b. Alternatively, electrode 5 and counterelectrode 6 can be arranged in drug containing elements 7a and 7b, as it is shown in FIG. 20.

Figure 21:
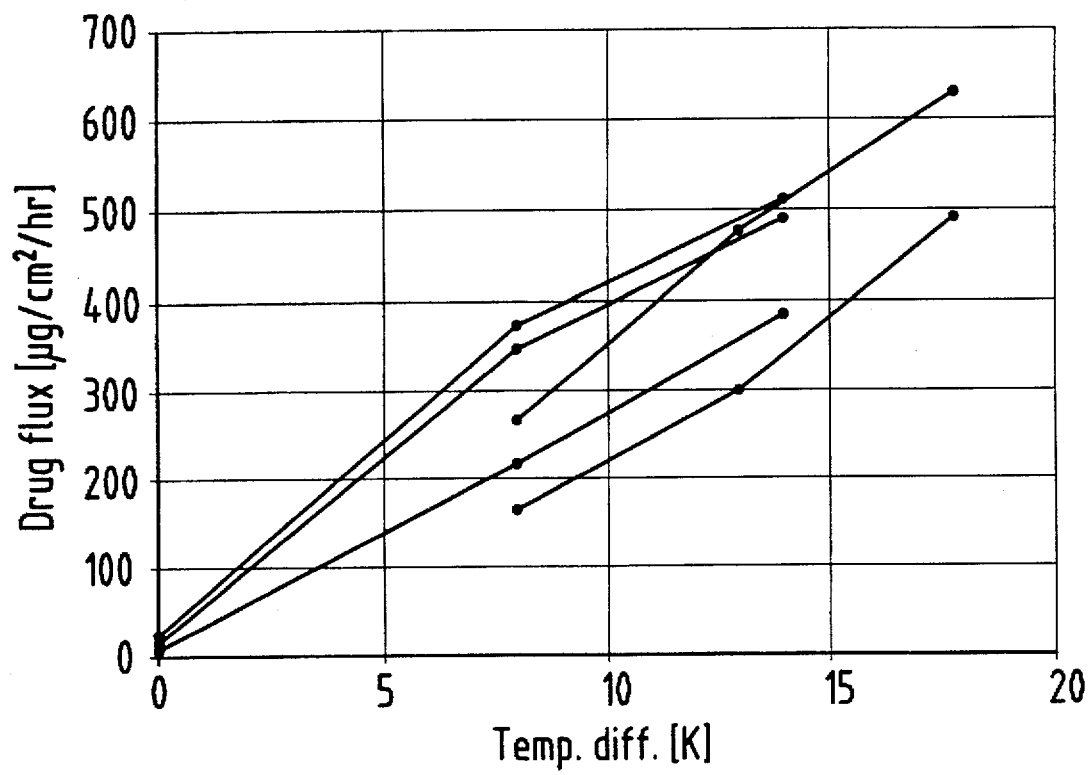
FIG. 21 is a graphical representation of how drug flux varies with thermopile temperature difference.

To determine how drug flux changes with thermopile temperature differences, a piece of human cadaver skin was fixed between the two chambers of a diffusion cell. In the chambers, Ag/AgCl electrodes were inserted and connected to the thermopile outputs. The thermopile was of the type represented in FIG. 2 and was clamped between two metal plates, which were kept at different temperatures. In the donor chamber, the drug was present, which had a net charge of −1. The donor electrode in the donor chamber was connected to the negative output lead of the thermopile. The results of several experiments with different temperature differences over the thermopile are compiled in FIG. 21. The graph clearly indicates that the flux increases roughly linearly with the temperature difference. Since the drug is very potent, therapeutic levels were easily obtained with a temperature difference of eight degrees centigrade. Although the thermopile output current may be lower when the thermopile is applied to the human skin rather than clamped between two metal plates, the feasibility of thermopile powered drug delivery is clearly demonstrated by FIG. 21.

If desired, an electronic control unit can be implemented in order to aid the drug delivery by controlling the power supply. This can be desirable, for instance, in order to start the delivery process by switching on the power supply, to control the delivery rate by controlling the supplied voltage or current, to increase or to decrease the supplied voltage or current in order to obtain desired dosage profiles, or to switch off the power supply after a desired dose has been delivered. Particularly, such an electronic circuit may be employed to compensate for the variations in output voltage or current due to temperature fluctuations or to convert the varying thermopile output voltage into a constant or a pulsed voltage or current.

In the case a transdermal system is powered by one or more silicon thermopiles (see FIGS. 10–13), it would be possible to integrate the control electronics in the silicon thermopile, preferentially in its thick rim. The approach of integrating electronics in the silicon thermopile structure is well known from silicon thermopile technology.

An endo- or exothermic process or reaction may be used to enhance the performance of the drug delivery system. The process would preferably take place at the location of the thermopile that is exposed to the ambient air and may be used to decrease or increase the temperature at this location distal from the skin. An example for an endothermic process is the evaporation of water or ethanol. This endothermic process results in the cooling of the location of the thermopile where the endothermic process takes place. In this way, it is assured that the side of the thermopile that is exposed to the ambient air is colder than the human skin and that such systems work even at high ambient temperatures. As a consequence the current only flows in one direction and the total current is higher than without the endothermic process. An example for an exothermic process is a chemical reaction during which heat is generated. Such processes are, for instance, applied in commercially available handwarmers. This exothermic process results in the heating of the location of the thermopile where the process takes place. In this way, it is assured that the side of the thermopile that is exposed to the handwarmer is warmer than the human skin and the system works even at low ambient temperatures. As a consequence the current only flows in one direction and the total current is higher than without the exothermic process. Other non-limiting examples of endo- and exothermic processes and reactions are the oxidation of iron or other metals, the dissolution of salts or other soluble materials in water or in another liquid and the neutralization process taking place when an acidic and a basic solution are mixed. By using such endo- or exothermic process which increases the output current of the thermopile, the drug flux may be increased.

Practically, a thermopile powered iontophoresis patch using evaporation of a liquid (with or without a rate controlling membrane) can be realized by using two release liners. The first release liner protects the drug containing element during storage and is removed prior to application of the patch. The second release liner would cover the back of the patch and inhibit the evaporation process during storage. It would be removed prior to application, which would start the endothermic process.

Another practical realization for incorporation of an endo- or exothermic process or reaction in a thermopile powered iontophoresis patch is to have the two reagents stored in two compartments separated by a seal. Upon application, the user would either remove or burst the seal, mix the two reagents and thus start the endo- or exothermic process or reaction. The use of a burstable seal for UATTS (User Activated Transdermal Therapeutic System) is well known from passive transdermal system technology (U.S. Pat. No. 4,917,676).

Figure 22:
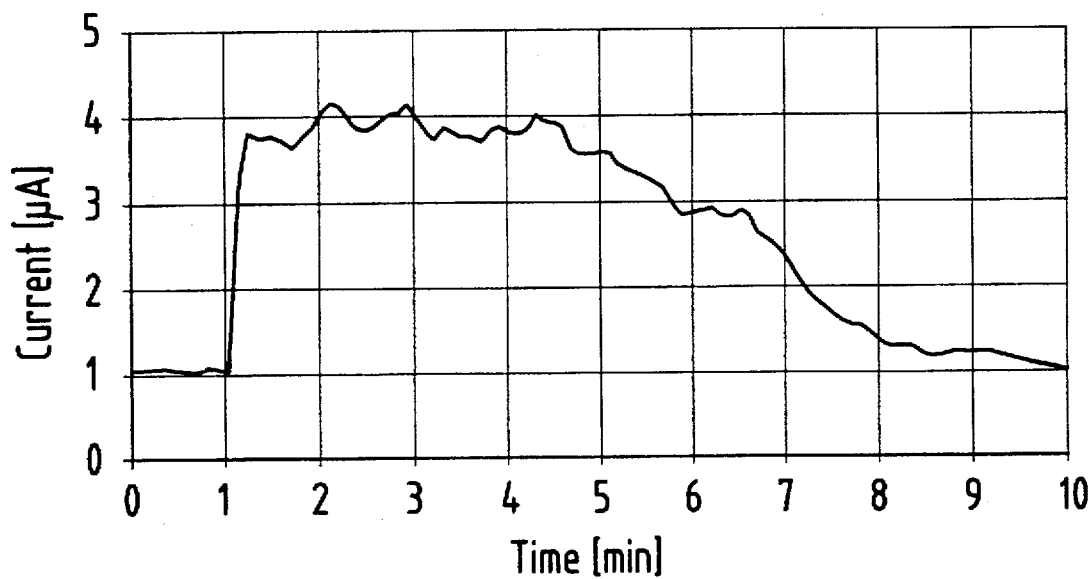
FIG. 22 is a graphical representation of how thermopile current output increases with the use of an endothermic process.

To demonstrate how thermopile current output increases with the application of an endothermic process, a thermopile, as represented in FIG. 2, was attached to the underarm of a human volunteer and the output leads were connected to a 12 k$\Omega$ resistor, which is an electrical representation of human skin. The ambient temperature was 20° C., the current through the resistor was measured during 10 minutes. After 1 minute, a small piece of regular paper (9×39 mm$^2$), which was soaked with water, was put on top of the thermopile. Due to evaporation of the water, the top side of the thermopile cooled down and the current through the resistor increased, as shown in FIG. 22. This experiment demonstrates that the use of an endothermic process can significantly increase the output current of a thermopile. It is clear to the skilled reader that other liquids could be used, and that a rate controlling membrane (known from passive transdermal therapeutic systems) could be used to control the rate of evaporation of the liquid and simultaneously form a drug containing element for the evaporation liquid. Likewise, other endothermic processes or reactions or exothermic processes or reactions could be employed to achieve an increased or decreased temperature at the side of the thermopile that is not in contact with the skin.

Virtually any therapeutic agent (drug) can be delivered using this transdermal device. The only limitation is that the drug have at least one form which may permeate through the skin and any barrier between the drug and the user's skin. The device is particularly useful for delivering agents requiring relatively non-specific entry to the body. This includes agents for which the dosage profile versus time and/or the total time required for the delivery of a certain dose are not critical. Furthermore, the device is suitable for the delivery of drugs requiring a low total dose to be delivered. This requirement can be met, for example, by potent drugs and/or by drugs having long biological half lives. Further, if no electronics are used, the therapeutic window should be relatively wide as the generated current may depend heavily on such factors as ambient temperature.

Non-limiting examples of drugs which may be delivered by the present device include Alzheimer's drugs such as arecoline and galanthamine; antitubercular agents, such as isoniazid and rifampin; analgesics, such as morphine, nicomorphine, buprenorphine, naloxone, sulfentanil, fentanyl, alfentanil, and sufentanyl; muscle relaxants, such as baclofen; β-andrenergic receptor agonists and antiasthmatics, such a theophylline, formoterol, albuterol and terbutaline; compulsive disorder drugs such as ritalin; steroids, such as melatonin, norethisterone acetate, prednisone, prednisolone, methyltestosterone, and desoxycorticosterone; anticholinergics, such as scopolamine and methscopolamine; vasodilators, such as priscoline; vasoconstrictors such as epinephrine and phenylephrine; antihypertensives, such as metoprolol; antihistamines, such as triprolidine, tripelenamine, and diphenhydramine; cholinergic agents, such as arecoline; CNS stimulants, such as methylphenidate and nikethimide; angiotensin converting enzyme inhibitors, such as enalapril, and benazepril;

nicotine, physotigmine, and naloxone; CNS agents such as bromocriptine, selfotel; serotoninergic agonists and antagonists; oligonucleotides, such as antisense agents; biomimetics; anti-inflammatory drugs such as diclofenac sodium, diclofenac potassium, and dexamethasone; impotence drugs such as yohimbine, prostaglandin E1, papaverine, phentolamine, and phenoxybenzamine; anti-cancer agents such as camptothecin, amsacrine, methotrexate, vinblastine, LH-RH agonists and hydroxy urea; and others as apparent to one of ordinary skill. Other drugs include amantadine, atropine, bromocritpine, caffeine, chlorpromazine, phloroquine, cimetidine, clonidine, diazepam, dobutamine, dopamine, fenoprofen, fluphenazine, flurazine, flurazepam, formoterol, imipramine, indomethacin, isoproterenol, levorphanol, lidocaine, mecamylamine, meperidine, minoxidil, nifedipine, parathyroid hormone (PHT 1-34); pindolol, prinomide, propanolol, promethazine, physostigmine, rifampin, salbutamol, salicylic acid, sufentanyl, terbutaline, theophylline, timolol, trimipramine, and verapamil.

A long biological half life can be achieved in situations in which the drug is absorbed into/onto an organ or tissue (bone, adipose tissue, etc.) from the systemic circulation quickly and subsequently released at a slower rate. In this case, that organ/tissue essentially acts as an internal drug reservoir, that is to say as a pharmacokinetic depot.

Another example of active agents to be delivered are vaccines. Upon penetration, vaccines use the systemic circulation as a pharmacokinetics compartment during the formation of antibodies. The dosing requirements are not stringent.

Further examples of active agents are insulin like growth factor (IGF) I and II. IGF delivery to skin and subcutaneous tissues may be achieved with iontophoresis. The skin, once loaded with IGF via iontophoresis, becomes the pharmacokinetics depot compartment.

Still further examples for drugs to be delivered are the class of bisphosphonates including 1-hydroxy-2-(imidazol-1-yl)ethane-1,1-diphosphonic acid (so-called Zoledronic acid) and 3-amino-1-hydroxypropane-1,1-diphoshphonic acid disodium salt (which is disodium salt of so-called pamidronic acid and which is registered to Ciba-Geigy Corporaation under the trademark Aredia®). The dosing requirements for Zoledronic acid are not stringent;the dosage profile and the total dose time are not critical. Also, the required dose is low. The described drug delivery device "dumps" the drug into the systemic circulation. Since Zoledronic acid is subsequently absorbed by the bones it has a very long half life. Therefore, in this example bone is the pharmacokinetics depot compartment.

While various embodiments have been described with reference to the drawings, many other variations will be apparent to those of ordinary skill in the art without departing from the spirit of the instant invention. The description of the embodiments is therefore only intended to illustrate the general concept underlying the instant invention and not to limit the scope of the invention.

We claim:

1. A transdermal drug delivery device comprising:
   a drug containing element selected from the group consisting of a reservoir, matrix, gel and nonwoven layer, said drug containing element comprising a drug;
   first and second electrodes for conducting a current flow through the drug containing element, the current flow causing the drug to be released from the drug containing element and to permeate through the skin of a user to which the device has been fixed;
   a power source connected to the first and second electrodes for providing the energy necessary to generate the current flow;
   wherein the power source comprises a thermocouple or thermopile comprising two poles which are connected to the first and second electrodes, the first pole being in contact with the user's skin and the second pole being in contact with the environment whereby a self-contained drug delivery device is formed which provides the energy necessary for generating the current flow by means of a difference in temperature of the skin of the user and the environment.

2. The device according to claim 1, wherein the power source is a thermopile comprising a series connection of two thermocouple elements arranged to form a column, the column of the elements being arranged between two rigid thermally conductive but electrically non-conductive plates.

3. The device according to claim 2, wherein one plate is arranged to come into contact with the skin of the user when the device is applied while the other plate is arranged to contact the environment, and wherein one pole of the thermopile is connected to the first electrode which is located in electrical contact with the drug containing element, while the other pole of the thermopile is connected to the second electrode.

4. The device according to claim 3, wherein two drug containing elements are provided, one of them being provided with the first electrode and the other being provided with the second electrode, and wherein one pole of the thermopile is connected to the first electrode while the other is connected to the second electrode.

5. The device according to claim 2, wherein the first electrode comprises an electrically as well as thermally conductive material, and wherein the first electrode is located on top of the thermally conductive drug containing element, wherein further one plate of the thermopile is arranged to be in contact with the first electrode, while the other plate is arranged to be in contact with the environment.

6. The device according to claim 2, further comprising a second drug containing element and wherein one plate of the thermopile is arranged to come into contact with one drug containing element, which comprises a thermally conductive material while the other plate is arranged to contact the environment, and wherein one pole of the thermopile is connected to the first electrode which is arranged to be in electrical contact with one of the two drug containing elements, while the other pole of the thermopile is connected to the second electrode which is arranged to be in electrical contact with the other of the two drug containing elements.

7. The device according to claim 6, wherein the first electrode is provided either on top of or in one of the two drug containing elements while the second electrode is provided either on top of or in the other of the two drug containing elements.

8. The device according to claim 1, wherein the power source is a thermopile which comprises an alternating series connection of two thermocouple elements which are arranged in a snake manner on the surface of a flexible plate made of an electrically non-conductive material.

9. The device according to claim 8, wherein the first electrode is arranged to be in electrical contact with the drug containing element, and wherein the flexible plate is arranged such that a first side of the flexible plate where one of the poles is located is arranged on top of the drug containing element, which is made of a thermally non-conductive material, said pole being connected to the first electrode, while a second side of the flexible plate where the other pole is located is bent down to be in contact with the skin, said other pole being connected to the second electrode.

10. The device according to claim 9, wherein the first electrode is arranged either on top of or in the drug containing element.

11. The device according to claim 8, further comprising a second drug containing element, and wherein the first electrode is arranged on top of or in one of the two drug containing elements while the second electrode is arranged on top of or in the other of the two drug containing elements.

12. The device according to claim 8, wherein a supporting member is provided in close proximity to the drug containing element, on top of which the first side of the flexible plate, where one of the poles is located, is arranged.

13. The device according to claim 12, further comprising a second drug containing element, wherein further the first electrode is arranged on top of or in one of the two drug containing elements while the second electrode is arranged on top of or in the other of the two drug containing elements, and wherein one pole of the flexible plate is connected to the first electrode while the other is connected to the second electrode.

14. The device according to claim 12, wherein the supporting member is made of a thermally conductive material, and wherein further the flexible plate is arranged such that the first side of the flexible plate, where one of the poles is located, is arranged on top of one of the drug containing elements which comprises a thermally non-conductive material, this pole being connected to the first electrode, and the second side of the plate, where the other pole is located, is arranged on top of the thermally conductive supporting member, thereby eliminating the need of bending the flexible plate.

15. The device according to claim 12, wherein the supporting member is made of a thermally non-conductive material, and wherein further the flexible plate is arranged such that the first side of the flexible plate, where one of the poles is located, is arranged on top of one of the drug containing elements which comprises a thermally conductive material, this pole being connected to the first electrode, and the second side of the plate, where the other pole is located, is arranged on top of the thermally non-conductive supporting member, thereby eliminating the need of bending the flexible plate, or the first side of the plate is bent down to be in contact with the skin.

16. The device according to claim 8, wherein the plate containing the snake thermopile is made of a non-flexible material and comprises a rim at a first edge portion thereof and a cantilever having a tip extending to the opposite side portion, the cantilever being mechanically connected to said first edge portion of the rim, wherein further a gap is provided between the cantilever tip and the other three edge portions of the rim, the thermocouples having one edge located on the rim and the other edge located near the tip of the cantilever.

17. The device according to claim 16, wherein the tip of the cantilever is connected via a thermally conductive piece to a thermally conductive sheet arranged above the plate, the rim of the plate being arranged to be in contact with the skin while the thermally conductive sheet is arranged to be in contact with the environment.

18. The device according to claim 16, wherein two plates are arranged such that the rim of the first plate is arranged to be in contact with the skin while the cantilever of the first plate is connected via a thermally conductive piece to the cantilever of the second plate, which is arranged above the first plate and wherein the rim of the second plate is connected to a thermally conductive sheet which is arranged above the second plate, the thermally conductive sheet being in contact with the environment.

19. A process of increasing drug flux from the device according to claim 1 comprising applying an endothermic process or reaction to cool down the pole which is in contact with the environment.

20. A process of increasing drug flux from the device according to claim 1 comprising applying an exothermic process or reaction to heat up the part of the pole which is in contact with the environment.

* * * * *